US 9,820,869 B2

(12) United States Patent  (10) Patent No.: US 9,820,869 B2
Aryan  (45) Date of Patent: Nov. 21, 2017

(54) INTERVERTEBRAL PRESSURE MONITOR

(71) Applicant: Henry E. Aryan, Fresno, CA (US)

(72) Inventor: Henry E. Aryan, Fresno, CA (US)

( * ) Notice: Subject to any disclaimer, the term of this patent is extended or adjusted under 35 U.S.C. 154(b) by 0 days.

(21) Appl. No.: 14/873,439

(22) Filed: Oct. 2, 2015

(65) Prior Publication Data

US 2017/0095343 A1    Apr. 6, 2017

(51) Int. Cl.
*A61F 2/46* (2006.01)
*A61F 2/44* (2006.01)
*A61B 17/02* (2006.01)

(52) U.S. Cl.
CPC .......... *A61F 2/4611* (2013.01); *A61B 17/025* (2013.01); *A61F 2/4455* (2013.01); *A61F 2/4657* (2013.01); *A61F 2002/4629* (2013.01); *A61F 2002/4666* (2013.01)

(58) Field of Classification Search
CPC ............... A61F 2/4611; A61F 2/4455; A61F 2002/4475; A61F 2002/4666; A61F 2/4657; A61F 2017/0256; A61B 2017/0256
See application file for complete search history.

(56) References Cited

U.S. PATENT DOCUMENTS

| | | | |
|---|---|---|---|
| 5,456,724 A | 10/1995 | Yen | |
| 6,706,005 B2 | 3/2004 | Roy | |
| 7,691,130 B2 | 4/2010 | Bruneau | |
| 7,901,440 B2 | 3/2011 | Ibrahim | |
| 8,197,488 B2 | 6/2012 | Sorrenti | |
| 8,202,299 B2 | 6/2012 | Wang | |
| 8,278,941 B2 | 10/2012 | Kroh | |
| 8,636,746 B2 | 1/2014 | Jimenez | |
| 8,771,360 B2 | 7/2014 | Jimenez | |
| 8,932,302 B2 | 1/2015 | Jimenez | |
| 2003/0135217 A1 | 7/2003 | Buttermann | |
| 2003/0236472 A1* | 12/2003 | Van Hoeck | A61B 17/0206 600/587 |
| 2004/0133132 A1 | 7/2004 | Chappuis | |
| 2005/0061086 A1 | 3/2005 | Chappuis | |
| 2005/0273170 A1* | 12/2005 | Navarro | A61F 2/442 623/17.13 |

(Continued)

OTHER PUBLICATIONS

Aryan, Henry E., et al., "Relaxation of Forces Needed to Distract Cervical Vertebrae After Discectomy", J Spinal Discord Tech, vol. 22, No. 2, Apr. 2009.

(Continued)

*Primary Examiner* — Julianna N Harvey
(74) *Attorney, Agent, or Firm* — GSS Law Group (57) ABSTRACT

An instrumented distractor includes a force sensor for measuring a force exerted by opposing surfaces of adjacent vertebrae pressing against fixed and adjustable arms on the distractor. The force on the distractor may be measured by a data acquisition system (DAS). An instrumented cage including at least one force sensor may be inserted into the same intervertebral space as the distractor and a measurement of force on the cage made by the DAS. A size and shape of the instrumented cage are preferably selected such that the magnitude of force on the cage is less than or equal to the magnitude of force measured with the distractor. In some embodiments, a first DAS is included in the instrumented distractor and a second DAS is included in the insertion handle, and the two data acquisition systems may communicate measured force values with one another.

16 Claims, 8 Drawing Sheets

(56) References Cited

U.S. PATENT DOCUMENTS

| | | | |
|---|---|---|---|
| 2006/0247773 A1* | 11/2006 | Stamp | A61B 5/076 623/17.11 |
| 2007/0239165 A1* | 10/2007 | Amirouche | A61B 5/1121 606/86 R |
| 2008/0177298 A1 | 7/2008 | Zucherman | |
| 2009/0012372 A1* | 1/2009 | Burnett | A61B 5/076 600/300 |
| 2010/0179558 A1 | 7/2010 | Quirno | |
| 2010/0274298 A1 | 10/2010 | Schiff | |
| 2011/0118794 A1 | 5/2011 | Pepper | |

OTHER PUBLICATIONS

Defino, Hla, et al., "Compression or distraction forces appliedon a pedicular fixation system: an experimental study", 2006, Acta Ortop Bras 14(3): 148-151.

D'Lima, DD, et al., "Implantable sensor technology: measuring bone and joint mechanics of daily life in vivo", Jan. 2013, Arthritis Research and Therapy, 15:203.

Kettler, A. "Can a modified interspinous spacer prevent instability in axial rotation and lateral bending?", 2008, Clinical Biomechanics, 23: 242-247.

Ledet, EH, et al., "Real-time in vivo loading in the lumbar spine: part 1. Interbody implant: load cell design and preliminary results", Oct. 2000, Spine, 25(20):2595-2600 (Abstract).

Ledet, EH, et al., "Direct real-time measurement of in vivo forces in the lumbar spine", 2005, Spine J, 5(1):85-94 (Abstract).

Rohlmann, A. et al. "Activities of everyday life with high spinal loads", May 2014, PLOS One, vol. 9, Issue 5.

Rohlmann, A. et al., "Monitoring the load on a telemeterised vertebral body replacement for a period of up to 65 months", Oct. 2010, Eur Spine J, 22:2575-2581.

Rohlmann, A. et al., "Spinal loads during post-operative physiotherapeutic exercises", Jul. 2014, PLOS One, vol. 9, Issue 7.

Rohlmann, A., et al., "Loads on a spinal implant measured in vivo during whole-body vibration, Jul. 2010,", Eur Spine J, vol. 19, Issue 7, pp. 1129-1135 (Abstract).

Seung Man Ha, "Vertebral distraction during anterior cervical discectomy and fusion causes postoperative neck pain", 2013, J Korean Neurosurg Soc, (53):288-292.

Svivek, J, et al., "An implantable strain measurement system designed to detect spine fusion", 2002, Spine vol. 27, No. 5, pp. 487-497.

Svizek, J, et al., "In vivo strain measurements for hardware and lamina during spine fusion", Nov. 2005, J Biomed Mat Res B Appl Biomater, 75(2), 243-50 (Abstract).

\* cited by examiner

INTERVERTEBRAL PRESSURE MONITOR

FIELD OF THE INVENTION

Embodiments are related to surgical devices and more particular to devices for achieving fusion of bones or pieces of bone.

BACKGROUND

Vertebrae in a spinal column are separated from one another by intervertebral discs that cushion the vertebrae and enable the spinal column to bend and twist. Mechanical stress and disease may cause damage to discs and vertebrae, possibly reducing intervertebral spacing, causing back pain, and reducing a range of motion for the spine. Pain, and possibly neurologic injury, may be caused by bone spurs forming on vertebral surfaces, by disc material herniating into the spinal canal, or for other reasons.

Surgical treatment to relieve pain and restore patient mobility may include removal of spurs, removal of discs, and fusion of adjacent vertebrae. Vertebrae may be fused together to prevent relative motion between the vertebrae, set intervertebral spacing to a preferred value, restore the spine to a preferred curvature, and for other reasons. Fusion may be achieved by connecting the vertebrae to one another with plates, screws, or spacing devices referred to as cages, and by procedures to encourage bone to grow between and join together adjacent vertebrae. Graft material may be placed into intervertebral spaces to enhance fusion. A cage to be inserted into an intervertebral space may be formed with an aperture for holding graft material in place while bone grows between vertebrae. Cages and other hardware may be made from titanium, stainless steel, polyether ether ketone (PEEK), graphite, carbon fiber, or other strong, stiff materials capable of withstanding the mechanical stresses and chemical and biological agents found in a spinal column.

Cages and other devices may be selected to securely hold adjacent vertebrae at a preferred intervertebral separation distance until fusion is achieved. For example, a cage shape and size may be selected to restore intervertebral spacing to a condition close to the spacing that existed when two adjacent vertebrae were separated by a healthy, nondegenerate disc. The optimum shape and size of a cage may vary with position along a spinal column and from patient to patient. However, it may be difficult to match the size and shape of a cage to a specific spinal condition. A cage that is too small may migrate away from an intervertebral position selected during surgery or may interfere with the progress of bone growth for fusion. A cage that is too large may be difficult to insert in to an intervertebral space or may subside into adjacent vertebrae. A cage that is the wrong size may fail to alleviate pain or may lead to damage to bone or neurological tissue. Selecting a size and shape of cage that will neither migrate nor subside after surgery may require repeated medical imaging of the contact area between cage and vertebrae during surgery, and may require replacement of one cage with another of a different size or shape until a preferred intervertebral spacing and preferred contact between cage and bone is determined by a surgeon.

SUMMARY

An example of an apparatus in accord with an embodiment includes an instrumented cage for implantation between adjacent vertebrae in a spinal column. The instrumented cage may include a cage force sensor affixed to a cage body. The cage force sensor may be disposed to generate a first electrical signal corresponding to a first value of strain in the cage body in response to a magnitude of stress applied to the cage body. The instrumented cage may further include an insertion handle aperture formed in the cage body.

The example of an apparatus may further include an insertion handle. The insertion handle may include a hollow shaft attached to a handgrip. The hollow shaft may have an end shaped for a close sliding fit into the insertion handle aperture in the instrumented cage.

The example of an apparatus may further include an instrumented distractor. The instrumented distractor may include a fixed arm attached to a shaft, an adjustable arm movably coupled to the shaft, and a distractor force sensor attached to the shaft. The distractor force sensor may be disposed to generate a second electrical signal corresponding to a value of strain in the distractor in response to a magnitude of stress applied to the fixed arm and the adjustable arm.

The example of an apparatus may further include a data acquisition system adapted for electrical connection to the instrumented distractor and to the insertion handle. The data acquisition system may include an analog-to-digital converter for converting the first electrical signal and the second electrical signal to numerical values.

An example of a method in accord with an embodiment may include inserting an instrumented distractor into an intervertebral space between two adjacent vertebrae; adjusting the instrumented distractor to separate the two adjacent vertebrae by a preferred separation distance; measuring a first value of force exerted against the instrumented distractor by opposing surfaces of the adjacent vertebrae; replacing the instrumented distractor with an instrumented cage in the intervertebral space; and measuring a second value of force exerted against the instrumented cage by the opposing surfaces of the adjacent vertebrae.

BRIEF DESCRIPTION OF THE DRAWINGS

FIGS. 3-7 show examples of instrumented cages in accord with an embodiment.

DESCRIPTION

An example of an apparatus embodiment includes an instrumented cage, an insertion handle, an instrumented distractor, and at least one data acquisition system for measuring and monitoring forces exerted by opposing surfaces of adjacent vertebrae in a spinal column undergoing surgical procedures for fusion of vertebrae. Forces may be represented as a magnitude of pressure against parts of the distractor and cage or as a magnitude of strain in parts of the distractor and cage in response to stress applied to the distractor and cage by contact with external objects such as vertebrae. Pressure and/or strain values may be measured and displayed by the data acquisition system in near real-time as a surgeon adjusts the distractor or inserts a cage into a selected intervertebral space. Instrumented cages of different sizes and shapes may be provided to insure a close sliding fit between a selected cage and opposing surfaces of adjacent vertebrae, with a magnitude of force measured by an optimum instrumented cage preferably less than a magnitude of force measured by the distractor.

Embodiments are advantageous for selecting an optimum cage size and shape that are neither too large nor too small for a particular intervertebral space. In contrast to prior art methods, repeated medical imaging, for example x-ray imaging, and possibly repeated trials with different cage sizes and shapes, may not be required to select an optimum size and shape of instrumented cage for a particular spinal condition. Embodiments may therefore reduce patient exposure to x-rays and reduce surgical duration compared to previously known methods for evaluating cage size and placement.

Embodiments are readily adapted to different instrumented cage types and sizes, for example, but not limited to, TLIF, ALIF, ACD, banana TLIF, XLIF, and TPLIF instrumented cages. Embodiments may further be adapted to different distractor types, for example, but not limited to, Caspar pin distractors, pedicle screw head distractors, and other instruments designed to separate and/or hold adjacent bony surfaces.

All components of an embodiment which may come into contact with a patient during a surgical procedure may be made to withstand medical sterilization procedures. Electrical connections between components may be implemented with electrical connectors capable of forming liquid-tight connector pairs to prevent current leakage between electrical conductors, between electrical conductors and electrical ground, and between electrical conductors and parts of a human body.

Figure 1:
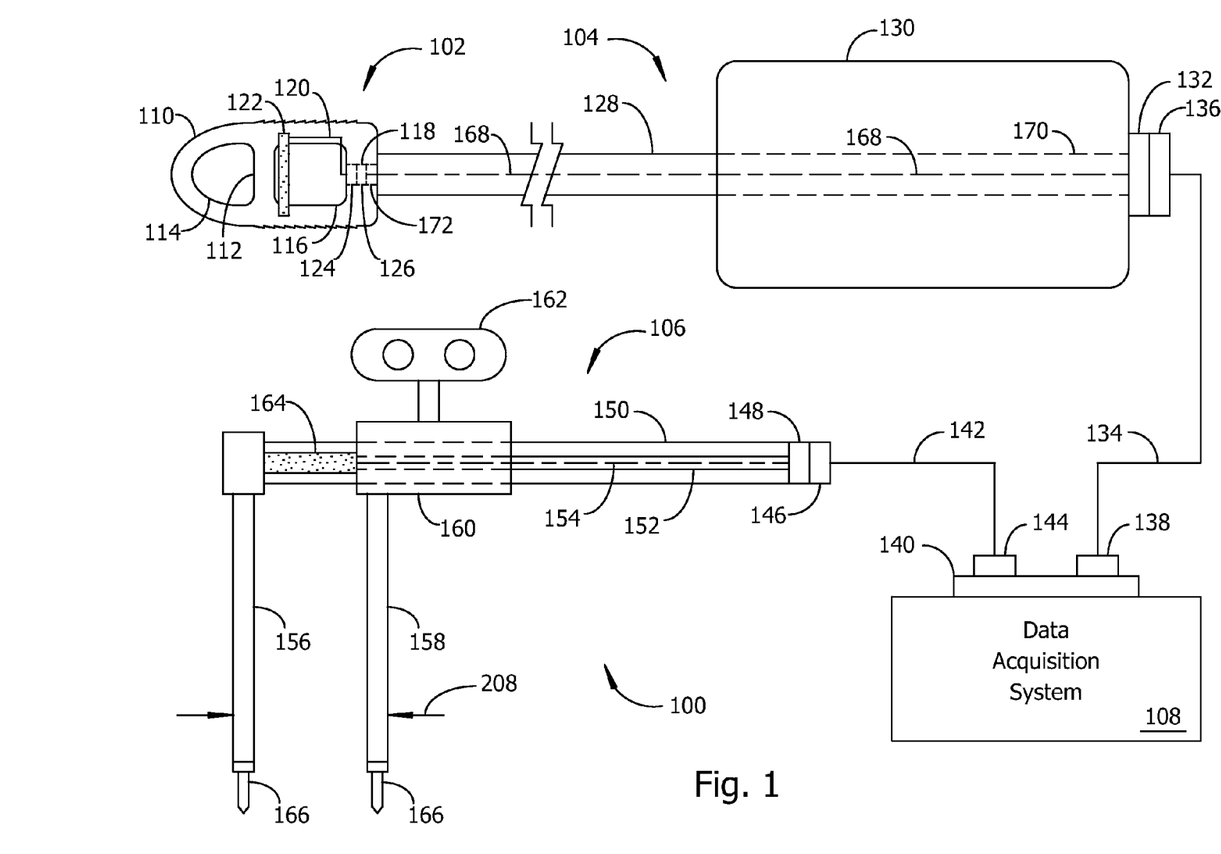
FIG. 1 is a schematic diagram of an example of an apparatus embodiment having an example of an instrumented transforaminal lumbar interbody fusion (TLIF) cage slidably coupled to an example of an insertion handle, an instrumented distractor, and a data acquisition system (DAS) for measuring and recording electrical signals from force and/or pressure sensors in the instrumented cage and instrumented distractor.

FIG. 1 shows a simplified schematic representation of an example of an apparatus embodiment 100 for selecting and inserting an optimum size of instrumented cage into an intervertebral space between two adjacent vertebrae in a spinal column after removal of an intervening disc. FIG. 1 illustrates an example of an instrumented cage 102 electrically and mechanically coupled to an insertion handle 104. The insertion handle 104 may be electrically connected by an insertion handle electrical cable 134 to an electrical connector 140 on a data acquisition system (DAS) 108. An instrumented distractor 106 may be electrically connected to the DAS 108 by a distractor electrical cable 142. The insertion handle 104 with its attached instrumented cage 102 and the instrumented distractor 106 may both be connected to the DAS 108 at the same time so that force measurements may be made without interrupting electrical connections to either the cage or the distractor. However, the insertion handle 104 and instrumented distractor 106 may be connected to the DAS 108 one at a time if a surgeon prefers.

The instrumented cage 102 in FIG. 1 is an example of an instrumented TLIF cage. The instrumented cage 102 may be formed with a web 112 connecting opposite sides of a cage body 110. The cage body 110 may be formed with one or more apertures which may be referred to as windows, for example a first window having an edge 114 and a second window having an edge 116. The cage body 110 may be formed with an insertion handle aperture 118 having a size and shape selected for a close sliding fit of an end 172 of a shaft 128 on the insertion handle 104.

An instrumented cage 102 in accord with an embodiment includes at least one cage force sensor 122. A cage force sensor 122 may generate an electrical signal having an amplitude related to a magnitude of force applied to part of the cage body 110. A cage force sensor 122 may alternatively sense another physical parameter that may be related to a magnitude of force acting on the cage body, for example a displacement of part of the cage body toward another part of the cage body or a measurement of strain in part of the cage body resulting from a stress applied to the cage body. Examples of a cage force sensor include, but are not limited to, a strain gauge, a linear variable differential transformer (LVDT), a differential variable reluctance transducer (DVRT), a load cell, and a pressure sensor. In some embodiments the cage force sensor 122 is attached to a web or a side wall of the cage body. A cage force sensor may alternatively be positioned to span a gap, for example a window in the cage body.

Electrical conductors 120 carry electrical signals between the cage force sensor 122 and a cage electrical connector 124 attached to the cage body 110. The cage electrical connector 124 may be connected mechanically and electrically to a corresponding electrical connector 126 on the shaft 128 of the insertion handle 104 when the end 172 of the shaft is inserted into the aperture 118 in the cage body. Electrical conductors 168 in the insertion handle may pass through the hollow shaft 128 and through an aperture 170 in the handgrip 130 of the insertion handle 104 to a connector 132 attached to the handgrip. The insertion handle cable 134 includes a first electrical connector 136 for connecting to corresponding connector 132 on the insertion handle and a second electrical connector 138 for carrying electrical signals from the cage force sensor 122 to an input connector 140 on the DAS 108.

An instrumented distractor 106 may be provided to establish a preferred intervertebral separation distance following disc removal. In the example of FIG. 1, the instrumented distractor 106 includes a fixed arm 156 attached to a distractor shaft 150. An adjustable arm 158 may be attached to an adjustment mechanism 160 that movably engages with the distractor shaft 150. A separation distance between the adjustable arm 158 and the fixed arm 156 may be set by operating an adjustment actuator 162. Examples of an adjustment mechanism 160 include, but are not limited to, a rack and pinion mechanism, a ratchet and pawl mechanism, and a friction drive wheel engaging a bearing surface. When the fixed arm and adjustable arm are placed in contact with opposing surfaces of an adjacent pair of vertebrae, increasing a separation distance between the arms may generally cause an increase in the magnitude of the force 208, and decreasing the separation distance may generally cause a decrease in the magnitude of the force.

A distractor force sensor 164 may be coupled to the distractor shaft 150 and optionally to the adjustment mechanism 160 or adjustable arm 158 to generate an electrical signal corresponding to the force 208. Examples of a distractor force sensor 164 include, but are not limited to, a strain gauge, a linear variable differential transformer (LVDT), a differential variable reluctance transducer (DVRT), a load cell, and a pressure sensor.

The distractor force sensor 164 may be electrically connected by electrical conductors 154 to an electrical connector 148 on the distractor 106. The electrical conductors 154 may optionally be positioned in a channel 152 formed in the distractor shaft 150. The electrical connector 148 on the distractor may couple to an electrical connector 146 on the distractor electrical cable 142. Another electrical connector 144 on the distractor electrical cable 142 may be connected to the DAS connector 140 for coupling electrical signals between the DAS and the distractor force sensor.

As suggested in FIG. 1, the instrumented distractor 106 may optionally be used to position one or more Caspar pins 166 for attachment of the pins to vertebrae.

Figure 2:
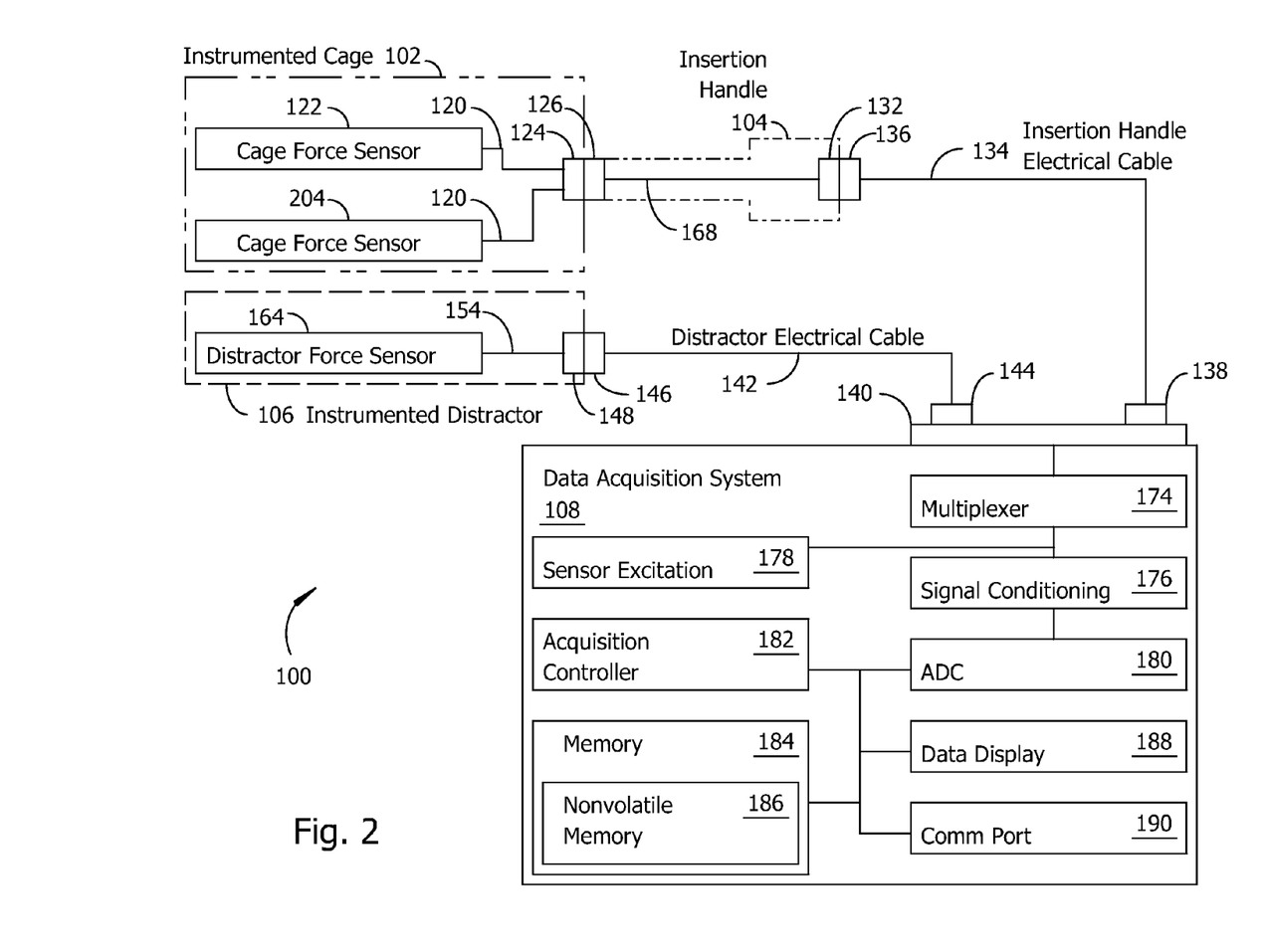
FIG. 2 is a schematic diagram illustrating an example of electrical and electronic components and electrical connections in accord with an embodiment, and further showing some details of a DAS in accord with an embodiment.

FIG. 2 shows some details of examples of a force measurement and force monitoring apparatus 100 with force sensors and a DAS 108. A multiplexer 174 couples input and output electrical signals through the DAS connector 140, for example electrical signals received from force sensors and optional sensor excitation signals generated by a sensor excitation circuit 178. A signal conditioning circuit 176 may convert input signals received from force sensors to a voltage signal having an amplitude selected for optimum resolution during signal conversion by an analog-to-digital converter (ADC) 180. In some embodiments, sensor excitation and signal conditioning may be combined, for example in a Wheatstone bridge. Other examples of signal conditioning circuits include, but are not limited to, a single-ended amplifier, a differential amplifier, a low-pass filter, and a high-pass filter.

Analog input signals to the ADC 180 may be converted to corresponding number pairs, each number pair representing a voltage value and a time value. Digitized data from the ADC 180 may be received by an acquisition controller 182, which may store the data in a memory 184, display the data on a data display 188, perhaps as a numerical value corresponding to a magnitude of measured force or as a graph showing changes in force values over time, and optionally output the digitized data on a communications port 190 for transmission to other devices. Part of the memory 184 accessibly coupled to the acquisition controller 182 may be in the form of nonvolatile memory 186. In some embodiments, each analog electrical signal input to the DAS 108 may be digitized by a separate ADC 180.

Figure 3:
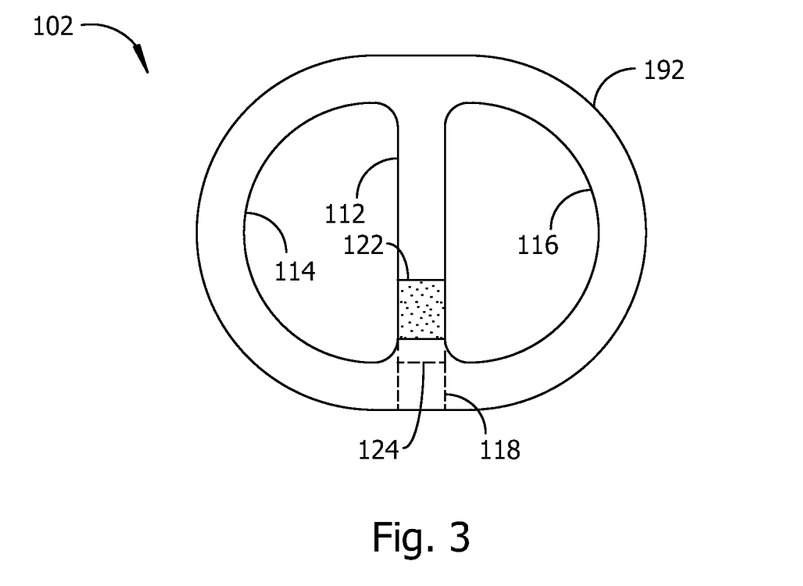
FIG. 3 is view toward a side of an example of an instrumented anterior lumbar interbody fusion (ALIF) cage.
Figure 4:
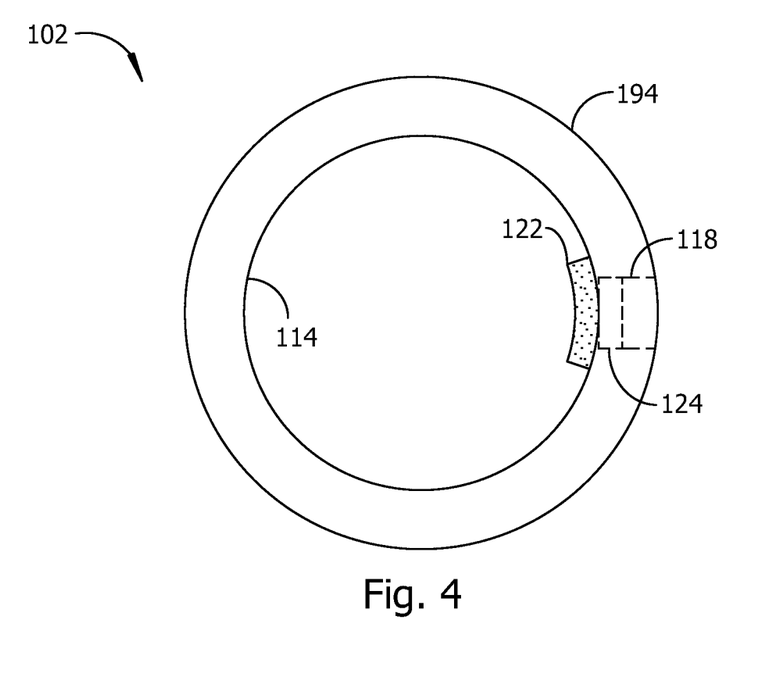
FIG. 4 is a view toward a side of an example of an instrumented anterior cervical discectomy (ACD) cage.
Figure 5:
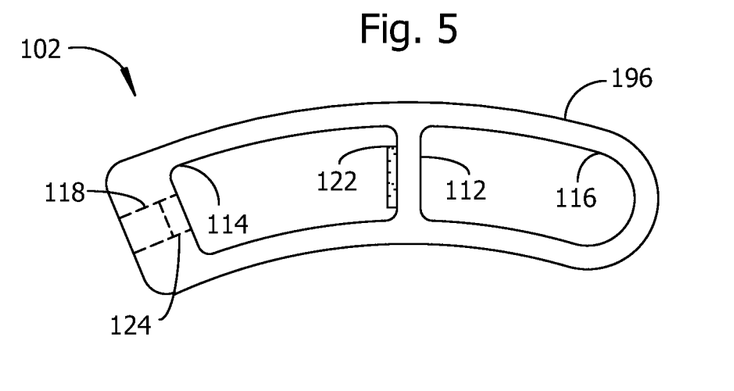
FIG. 5 is a view toward a side of an example of an instrumented banana-TLIF cage having sides with an arcuate shape.

FIG. 2 shows an example of an instrumented cage 102 with more than one cage force sensor, for example a first cage force sensor 122 and a second cage force sensor 204. Other examples of an instrumented cage 102 are shown in FIGS. 3-7. FIG. 3 shows an example of an instrumented ALIF cage 192 with a cage force sensor 122 affixed to a web 112. FIG. 4 shows an example of an instrumented ACD cage 194 with a cage force sensor 122 affixed to a side of the cage. FIG. 5 shows an example of an instrumented banana-TLIF cage 196 with a cage force sensor 122 affixed to a web 112.

Figure 6:
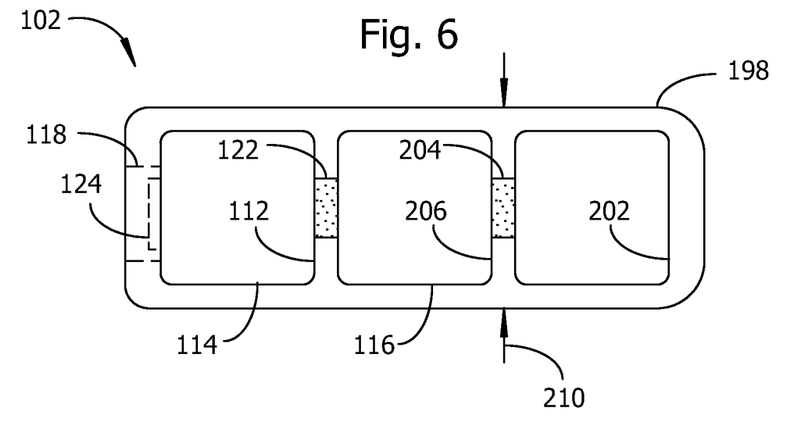
FIG. 6 is a view toward a side of an example of an instrumented extreme lateral interbody fusion (XLIF) cage having straight sides.
Figure 7:
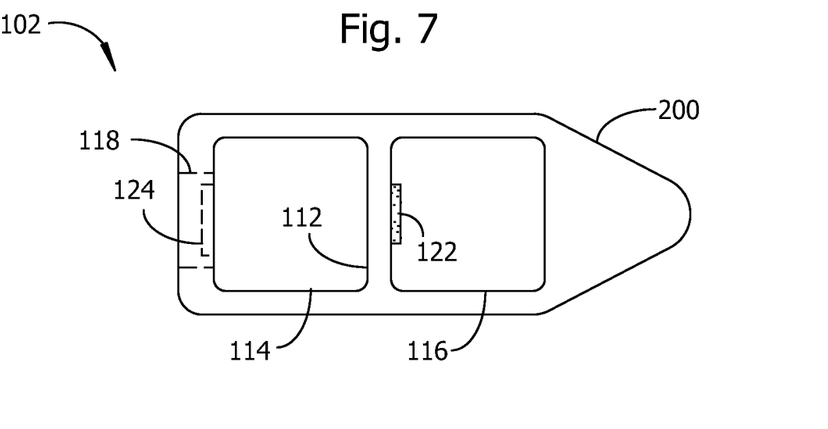
FIG. 7 is a view toward a side of another example of an instrumented TLIF cage which may be referred to as an instrumented transforaminal posterior lumbar interbody fusion (TPLIF) cage.

FIG. 6 shows an example of an instrumented cage 102 formed as an XLIF cage 198. The XLIF cage 198 includes a first web 112 and a second web 206 separating three windows, a first window having an edge 114, a second window having an edge 116, and a third window having an edge 202. A first cage force sensor 122 may be affixed to the first web 112. A second cage force sensor 204 may be affixed to the second web 206. A pair of opposing arrows 210 show an example of a compression force imposed on the cage, for example by close contact with vertebrae on either side of the cage. FIG. 7 shows an example of an instrumented TPLIF cage 200.

Figure 8:
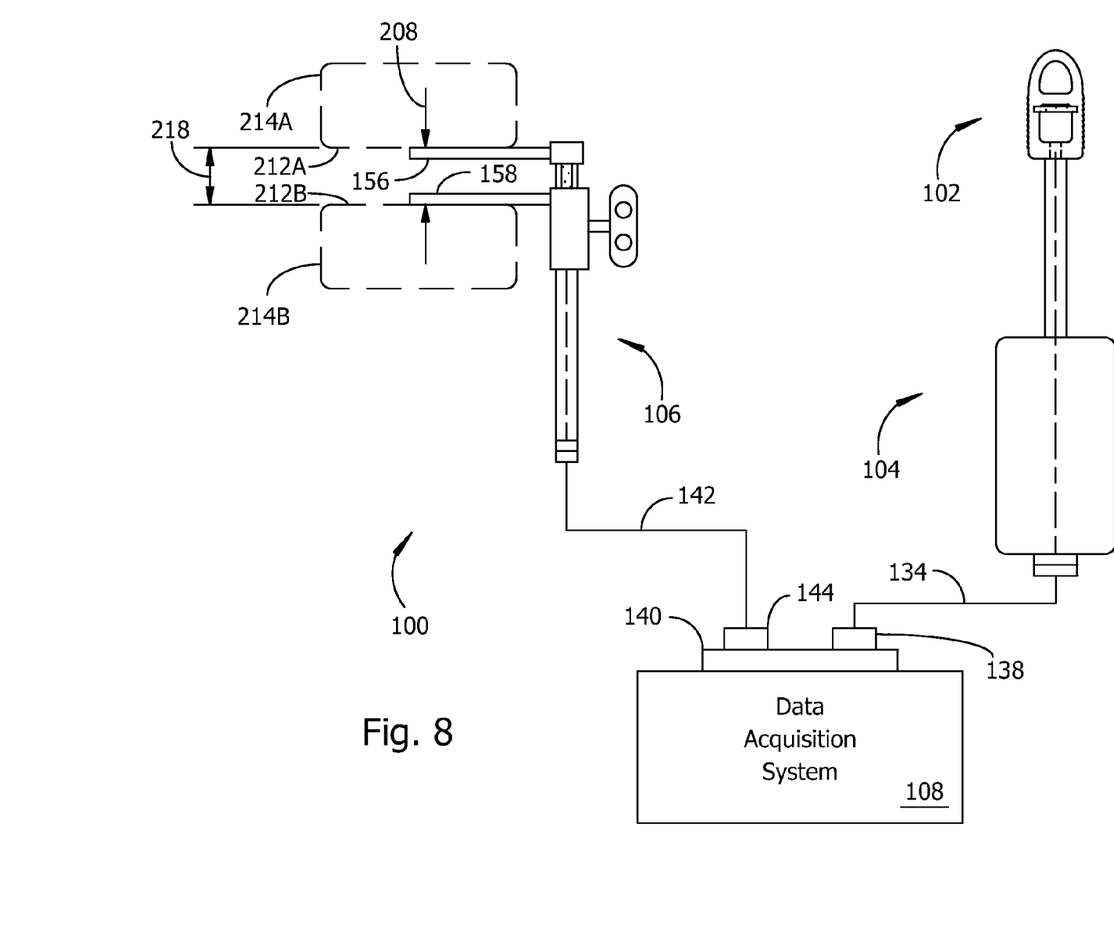
FIG. 8 is a schematic diagram of an example of a distractor embodiment disposed in an intervertebral space between opposing surfaces on two adjacent vertebrae in a spinal column.
Figure 9:
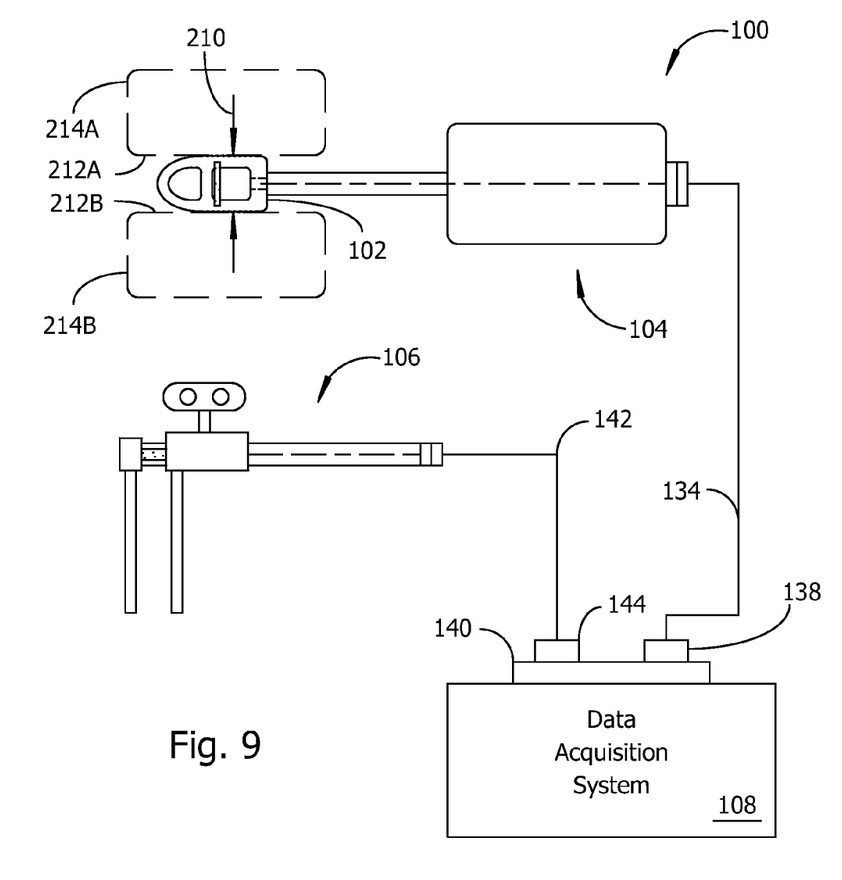
FIG. 9 continues the example of FIG. 8, with the example of a distractor removed from the intervertebral space and an example of an instrumented cage inserted into the intervertebral space.

FIGS. 8-9 illustrate examples of an apparatus embodiment interacting with examples of adjacent vertebrae in a spinal column. In the example of FIG. 8, the fixed arm 156 and adjustable arm 158 of the instrumented distractor 106 are in firm contact with opposing surfaces (212A, 212B) on adjacent vertebrae (214A, 214B). The instrumented distractor 106 may be adjusted to separate the opposing surfaces (212A, 212B) to a preferred separation distance 218 in the intervertebral space. A preferred separation distance may be selected to alleviate pain, to induce a preferred degree of curvature in a spinal column, to reduce degradation of discs in the spinal column, to provide space for insertion of an instrumented cage, or for other reasons. Measurements of a force imposed on the opposing surfaces of the vertebrae by the fixed and adjustable arms of the instrumented distractor, equal in magnitude and opposite in algebraic sign to the force 210 imposed on the distractor arms by the vertebrae, may be made by the DAS 108 in near-real-time as the distractor is adjusted. Displayed force measurements may assist a surgeon in selecting a preferred value of separation distance 218.

FIG. 9 continues the example of FIG. 8. In FIG. 9, the instrumented distractor has been removed from the intervertebral space and the instrumented cage 102 inserted in the same intervertebral space with the insertion handle 104. Electrical signals from the cage force sensor pass through the insertion handle and then into the DAS 108 as previously explained. The DAS 108 may send sensor excitation signals through the insertion handle to the cage force sensor. Measurements of a compression force 210 acting on the instrumented cage 102, equal in magnitude and opposite in algebraic sign to a force exerted on opposing faces of adjacent vertebrae by the arms on the distractor, may be made while the insertion handle is coupled to the instrumented cage. Measurements of the force 210 may be used to confirm proper size and placement of the instrumented cage 102 between adjacent vertebrae (214A, 214B). For example, it may be preferable to select an instrument cage large enough to firmly contact both opposing surfaces (212A, 212B) of the adjacent vertebrae (214A, 214B), but not so large that the measured force 210 is greater than the corresponding force measured when the instrumented distractor was placed between the vertebrae.

The DAS 108 may display status messages comparing the force 208 measured with the instrumented distractor 106 to the force 210 measured with the instrumented cage 102. For example, a status message may indicate that a force 210 for a cage is too low compared to the force 208 measured for the distractor 106, possibly suggesting that the cage is too small to be retained in the intervertebral without migration. Another example of a status message may indicate that a force 210 for the cage is too high, suggesting that the cage may be too large and may subside into vertebral surfaces 212. Another example of a status message may indicate that a force 210 is a preferred value less than or equal to the value of the force 208, suggesting that an optimum size of instrumented cage may have been placed in the intervertebral space.

Figure 10:
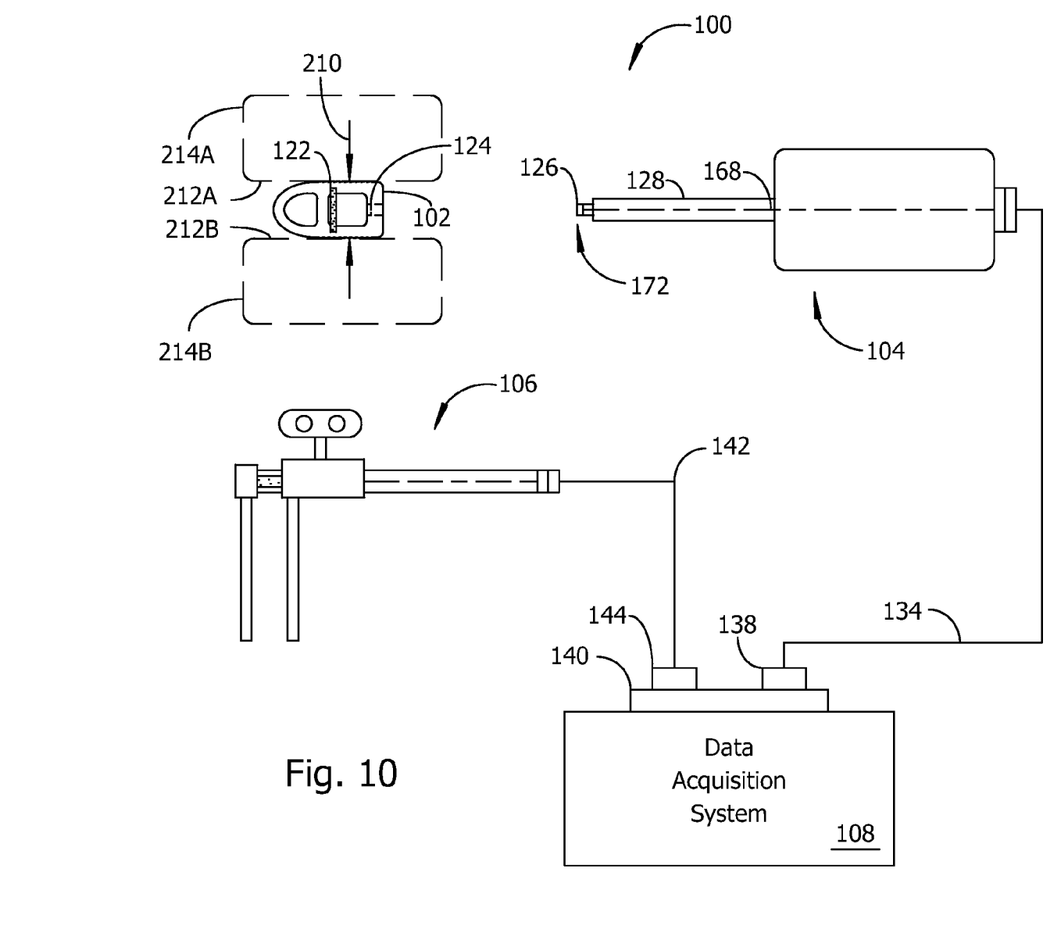
FIG. 10 continues the example of FIGS. 8 and 9, with the example of an insertion handle withdrawn from the example of an instrumented cage, interrupting electrical connections between the cage force sensor and the DAS and leaving the cage in firm contact with the two adjacent vertebrae.

After force measurements, visual inspection, and possibly medical imaging have been used to confirm proper size and placement of an instrumented cage between vertebrae, the end 172 of the insertion handle may be withdrawn from the instrumented cage 102 as suggested in FIG. 10. Withdrawing the insertion handle separates coupled electrical connectors (124, 126) and interrupts electrical connections between the instrumented cage 102 and the DAS 108. After the insertion handle 104 is withdrawn, the instrumented cage 102 may remain in place in the spinal column to facilitate fusion of vertebrae (214A, 214B) on either side of the cage.

Figure 11:
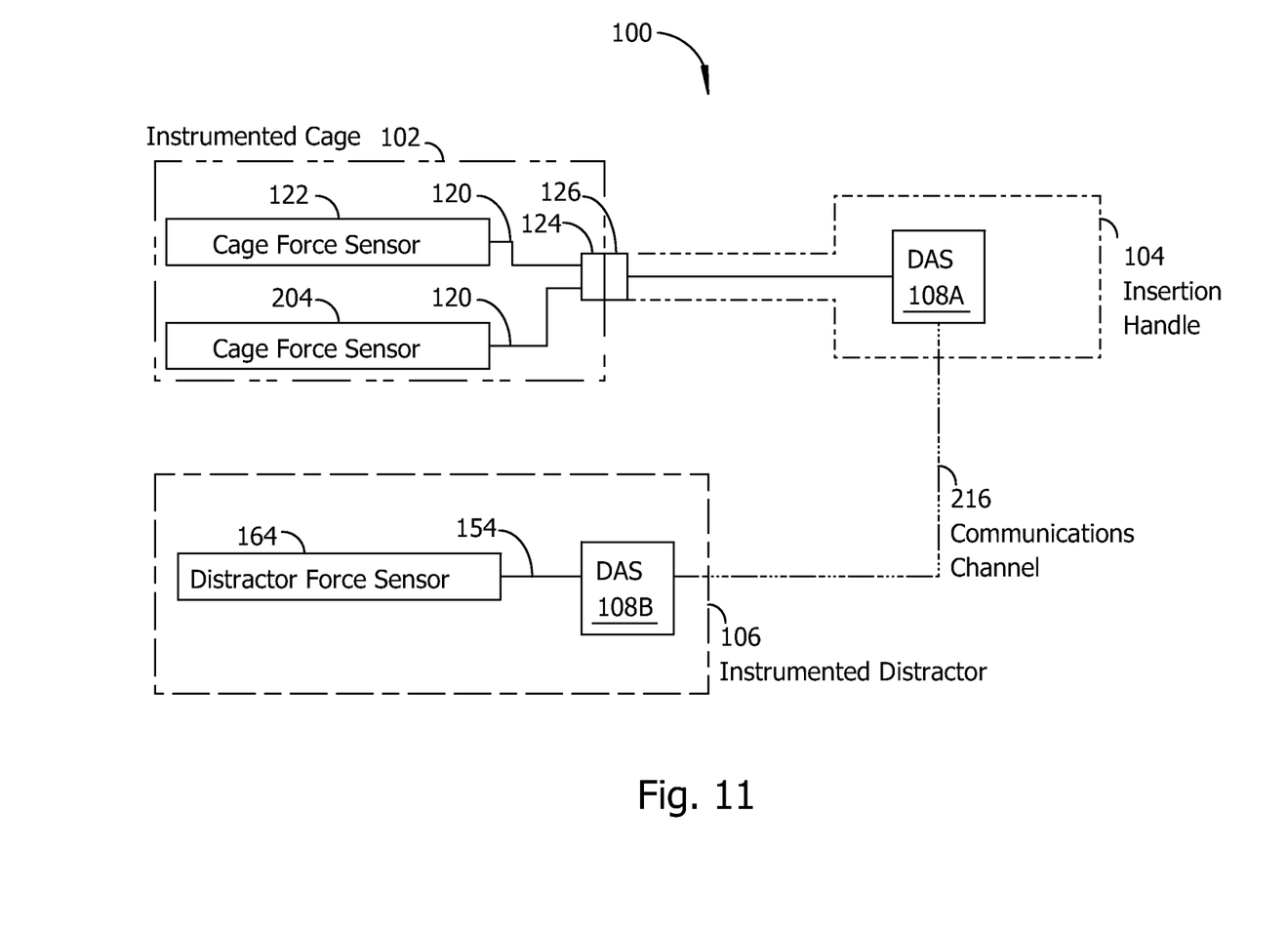
FIG. 11 is a schematic diagram of an alternative embodiment in which a first DAS is included with the insertion handle and a second DAS is included with the instrumented distractor.

In an alternative embodiment shown schematically in FIG. 11, a DAS 108 may be part of the insertion handle 104. For example, the parts of the DAS 108 shown in the example of FIG. 2 may be installed directly into the hand grip of the insertion handle, perhaps with the data display 188 visible from an outer surface of the hand grip. A second instance of the DAS 108 may optionally be installed in the instrumented distractor 106. The DAS 108A in the insertion handle and the DAS 108B in the instrumented distractor may optionally communicate with one another or with other communications-enabled systems over a communications channel 216. The communications channel 216 may be implemented as wired electrical connections or as wireless radio-frequency or optical signals.

An example of a method embodiment may include any one or more of the following steps:
inserting an instrumented distractor into an intervertebral space between two adjacent vertebrae;
adjusting the instrumented distractor to separate the two adjacent vertebrae by a preferred separation distance;
measuring a first value of force exerted against the instrumented distractor by opposing surfaces of the adjacent vertebrae;
replacing the instrumented distractor with an instrumented cage in the intervertebral space; and
measuring a second value of force exerted against the instrumented cage by the opposing surfaces of the adjacent vertebrae.

The example of a method embodiment may optionally include:
selecting the instrumented cage to be large enough to contact both opposing surfaces of the adjacent vertebrae; and
selecting the instrumented cage such that the second value of force is less than or equal to the first value of force.

Unless expressly stated otherwise herein, ordinary terms have their corresponding ordinary meanings within the respective contexts of their presentations, and ordinary terms of art have their corresponding regular meanings.

What is claimed is:

1. An apparatus, comprising:
an instrumented cage for implantation between vertebrae in a spinal column, comprising:
a cage body formed with a first window and a second window;
a web integrally joined to a first side of said cage body and to a second side opposite said first side, said web intervening between said first window and said second window;
a cage force sensor affixed to said web, said cage force sensor disposed to generate a first electrical signal corresponding to a value of strain in said web in response to a force applied to said first and second sides of said cage body by said vertebrae; and
an insertion handle aperture formed in said cage body;
an insertion handle, comprising:
a hollow shaft attached to a handgrip, said hollow shaft having an end shaped for a close sliding fit into said insertion handle aperture in said instrumented cage;
an instrumented distractor, comprising:
a fixed arm attached to a shaft;
an adjustable arm movably coupled to said shaft;
a distractor force sensor attached to said shaft, said distractor force sensor disposed to generate a second electrical signal corresponding to a value of strain in said shaft in response to a force applied to said fixed arm and said adjustable arm; and
a data acquisition system adapted for electrical connection to said instrumented distractor and to said insertion handle, comprising an analog-to-digital converter for converting said first electrical signal and said second electrical signal to numerical values,
wherein at least one of said first window and said second window in said cage body is a window for holding graft material.

2. The apparatus of claim 1, further comprising:
said cage body further comprising a cage electrical connector electrically connected to said cage force sensor;
said insertion handle further comprising:
a first insertion handle electrical connector attached to said end of said hollow shaft; and
a second insertion handle electrical connector attached to said handgrip and electrically connected to said first insertion handle electrical connector by conductors passing through said hollow shaft and said handgrip; and
said instrumented distractor further comprising a distractor electrical connector electrically connected to said distractor force sensor,
wherein said cage electrical connector, said first insertion handle electrical connector, said second insertion handle electrical connector, and said distractor electrical connector are adapted to withstand medical sterilization procedures, and said first insertion handle electrical connector is adapted to form a liquid-resistant electrical connection with said cage electrical connector.

3. The apparatus of claim 1, wherein said instrumented distractor further comprises an adjustment mechanism coupled to said adjustable arm for moving said adjustable arm relative to said fixed arm.

4. The apparatus of claim 1, wherein said data acquisition system further comprises:
an acquisition controller electrically connected to said analog-to-digital converter;
a memory for storing said numerical values; and
a data display for displaying said numerical values.

5. The apparatus of claim 4, further comprising:
a multiplexer electrically connected to said acquisition controller; and
a signal conditioning circuit electrically connected to said multiplexer, said signal conditioning circuit adapted to convert said first and second electrical signals to voltage signals for input to said analog to digital converter.

6. The apparatus of claim 5, further comprising a sensor excitation circuit electrically connected to said multiplexer.

7. The apparatus of claim 1, wherein said apparatus comprises a separate analog to digital converter for each of said first and second electrical signals.

8. The apparatus of claim 1, wherein said instrumented distractor is a Caspar pin distractor.

9. The apparatus of claim 1, wherein said instrumented cage is formed as an anterior lumbar interbody fusion (ALIF) cage.

10. The apparatus of claim 1, wherein said instrumented cage is formed as a posterior lumbar interbody fusion (PLIF) cage.

11. The apparatus of claim 1, wherein said instrumented cage is formed as an extreme lateral interbody (XLIF) cage.

12. The apparatus of claim 1, wherein said instrumented cage further comprises a second cage force sensor attached to said cage body, and said second cage force sensor is coupled to said data acquisition system.

13. The apparatus of claim 1, wherein said cage force sensor extends across said first window in said instrumented cage.

14. The apparatus of claim 1, wherein said data acquisition system is a first data acquisition system electrically connected to said insertion handle, and further comprising a second data acquisition system electrically connected to said instrumented distractor.

15. The apparatus of claim 14, wherein said first data acquisition system is electrically connected by a communications channel to said second data acquisition system.

16. The apparatus of claim 1, wherein said cage body is a transforaminal lumbar interbody fusion cage.

\* \* \* \* \*